[19] United States Patent
Wierenga et al.

[11] 4,308,272
[45] Dec. 29, 1981

[54] PROCESS FOR TREATING HYPERTENSION

[75] Inventors: Wendell Wierenga; Harvey I. Skulnick, both of Kalamazoo, Mich.

[73] Assignee: The Upjohn Company, Kalamazoo, Mich.

[21] Appl. No.: 193,573

[22] Filed: Oct. 3, 1980

[51] Int. Cl.³ ............................................ A61K 31/505
[52] U.S. Cl. .................................................... 424/251
[58] Field of Search ........................................ 424/251

[56] References Cited

U.S. PATENT DOCUMENTS

| 2,704,285 | 3/1955 | Rorig | 260/256.4 |
| 2,723,777 | 11/1955 | Grüssner et al. | 260/343.2 |
| 2,776,283 | 1/1957 | Rorig | 260/247.5 |
| 3,956,302 | 5/1976 | Hunter et al. | 260/256.4 |

FOREIGN PATENT DOCUMENTS 1223686 3/1971 United Kingdom .

OTHER PUBLICATIONS

Nicols, Weed and Underwood, Antimicrobial Agents, Chemo. Ther. 9 433, (1976).
Brown and Stevens, JCS Perkin I, 1023, 1975.
Sirakawa, Yakugaku Zasshi 80, 1542, 1960, CA 55, 10651b.
Kulkarni et al., J. Sci. and Ind. Research (India), 19C, 6–8 (1960), CA 54, 22576C.

Primary Examiner—Stanley J. Friedman
Attorney, Agent, or Firm—John J. Killinger

[57] ABSTRACT

A process for treating hypertension comprising the systemic administering to a hypertensive subject a compound of the formula:

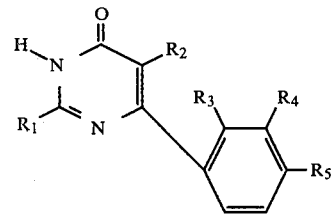

wherein
$R_1$ is —$NH_2$.
$R_2$ is chloro, bromo, or iodo.
$R_3$ is hydrogen or fluorine.
$R_4$ is hydrogen or fluorine, and
$R_5$ is hydrogen, fluorine, or $CH_3$; or the salts thereof in association with a pharmaceutical carrier.

3 Claims, No Drawings

PROCESS FOR TREATING HYPERTENSION

BACKGROUND OF THE INVENTION

The preparation and use of 2-amino-5-halo-6-alkyl-4-pyrimidinols as antiviral agents is known (U.S. Pat. No. 3,956,302, and Nicols, Weed and Underwood, Antimicrobial Agents, Chemo. Ther. 9 433, 1976). Preparation of 2-amino-5-bromo-6-phenyl-4-pyrimidinol (V, where $X_3$ is Br and $X_1$ is phenyl) has been reported (Brown and Stevens, JCS Perkin I, 1023, 1975) but no utility has been described for this material. Snell, Elias and Freeman in Great Britain Pat. No. 1,223,686 (1967) disclose a variety of 5,6-disubstituted 2-amino-4-pyrimidinols, such as 2-dimethylamino-5-bromo-6-methyl-4-pyrimidinol. Various 5-unsubstituted 2-amino-6-arylpyrimidinols are known (e.g., Sirakawa, Yakugaku Zasshi 80, 1542, 1960, CA 55, 10651b), Kulkarni et al., J. Sci and Ind. Research (India) 19C, 6–8 (1960), CA 54, 22576C and U.S. Pat. No. 2,776,283. Diuretics and cardioregulatory properties are described for various 2-amino and 2-substituted amino-5-aminomethyl and 5-aryl-6-aryl-4-pyrimidinols (U.S. Pat. Nos. 2,704,285, 2,723,777 and 2,776,283).

Compounds within the scope of the instant invention have been described in copending application Ser. No. 022,205, filed Mar. 19, 1979, and are useful as antiviral and interferon inducing agents, or the Belgian equivalent thereof, Belgian Pat. No. 882,315.

BRIEF DESCRIPTION OF THE INVENTION

This invention relates to the treatment of hypertension with a group of compounds having a unique combination of pharmacological activities, namely diuretic and antihypertensive activities both of which are desirable in healing hypertensive subjects.

DETAILED DESCRIPTION

The active compounds of the present invention are represented by the formula:

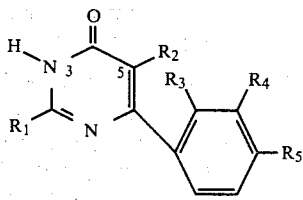

I wherein
$R_1$ is $-NH_2$.
$R_2$ is chloro, bromo, or iodo.
$R_3$ is hydrogen or fluorine.
$R_4$ is hydrogen or fluorine, and
$R_5$ is hydrogen, fluorine, or $CH_3$, including the salts thereof.

The compounds of the formula I can be prepared by methods known in the art, preferably by the improved method disclosed in copending application Ser. No. 022,205, filed Mar. 19, 1979, or the Belgian equivalent thereof, Belgium Pat. No. 882,315.

Suitable acid addition salts are acids having a pharmacologically acceptable anion. Suitable anions are, for example, chloride, sulfate, phosphate, nitrate, and the like. Suitable alkali metal or alkaline earth metal salts are bases having a pharmacologically acceptable cation. Suitable cations are for example lithium, sodium, potassium, ammonium and the like.

Illustratively, dosage levels of the administered active ingredients can be: intravenous, 0.1 to about 50 mg/kg; intraperitoneal, 0.1 to about 200 mg/kg; subcutaneous, 0.1 to about 150 mg/kg; intramuscular, 0.1 to about 150 mg/kg; orally, 0.1 to about 400 mg/kg; and preferably about 1 to 200 mg/kg; intranasal instillation, 0.1 to about 50 mg/kg; and aerosol, 0.1 to about 50 mg/kg; of animal (body) weight.

Expressed in terms of concentration, an active ingredient can be present in the compositions of the present invention for localized use about the cutis, intranasally, pharyngolaryngeally, bronchially, bronchiolially, intravaginally, rectally, or ocularly in a concentration of from about 0.1 to about 50% w/w of the composition; preferably about 1 to about 20% w/w of the composition; and for parenteral use in a concentration of from about 0.5 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelating solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and a polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and the concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred or by dry powder for insufflation.

The active ingredients can also be admixed in animal feed. The active ingredients can conveniently be prepared in the form of a food premix. The food premix can comprise an active ingredient in admixture with an edible pharmaceutical diluent such as starch, oatmeal, flour, calcium carbonate, talc, dried fish meal and the like nontoxic, orally acceptable pharmaceutical diluents. The prepared premix is then conveniently added to the regular feed.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as co-solvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets teaspoonfuls, tablespoonfuls, dropperfuls, ampuls, vials, segregated multiples of any of the foregoing, and other forms as herein described.

The active ingredients to be employed as antihypertensive agents can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

EXAMPLE 1: Hard Gelatin Capsules

One thousand two piece hard gelatin capsules for oral use, each capsule containing 100 mg of 2-amino-5-bromo-6-metafluorophenyl-4(3H)-pyrimidinone, are prepared from the following types and amounts of ingredients:

| | |
|---|---|
| 2-Amino-5-bromo-6-metafluorophenyl-4(3H)-pyrimidinone, micronized | 100 gm |
| Lactose | 100 gm |
| Corn starch | 20 gm |
| Talc | 20 gm |
| Magnesium stearate | 2 gm |

The 2-amino-5-bromo-6-metafluorophenyl-4(3H)-pyrimidinone finely divided by means of an air micronizer, is added to the other finely powdered ingredients, mixed thoroughly and then encapsulated in the usual manner.

The foregoing capsules are useful for preventing or treating hypertension by the oral administration of one or two capsules one to four times a day.

Using the procedure above, capsules are similarly prepared containing 2-amino-5-bromo-6-metafluorophenyl-4(3H)-pyrimidinone in 50 mg, 250 mg, and 500 mg amounts by substituting 50 gm, 250 gm, and 500 gm of 2-amino-5-bromo-6-metafluorophenyl-4(3H)-pyrimidinone for the 100 gm used above.

EXAMPLE 2: Soft Gelatin Capsules

One piece soft gelatin capsules for oral use, each containing 250 mg of 2-amino-5-bromo-6-metafluorophenyl-4(3H)-pyrimidinone (finely divided by means of an air micronizer), are prepared by first suspending the compound in 0.5 ml of corn oil to render the material capsulatable and then capsulating in the above manner.

The foregoing capsules are useful as antihypertensive agents by the oral administration of one or two capsules one to four times a day.

EXAMPLE 3: Tablets

One thousand tablets, each containing 500 mg of 2-amino-5-bromo-6-metafluorophenyl-4(3H)-pyrimidinone are prepared from the following types and amounts of ingredients:

| | |
|---|---|
| 2-Amino-5-bromo-6-metafluorophenyl-4(3H)-pyrimidinone, micronized | 500 gm |
| Lactose | 75 gm |
| Corn starch | 50 gm |
| Magnesium stearate | 4 gm |

| -continued | |
|---|---|
| Light liquid petrolatum, micronized | 5 gm |

The 2-amino-5-bromo-6-metafluorophenyl-4(3H)-pyrimidinone, finely divided by means of an air micronizer, is added to the other ingredients and then thoroughly mixed and slugged. The slugs are broken down by forcing through a number sixteen screen. The resulting granules are then compressed into tablets, each tablet containing 500 mg of 2-amino-5-bromo-6-metafluorophenyl-4(3H)-pyrimidinone.

The foregoing tablets are useful for treating hypertension by the oral administration of one or two tablets, one to four times a day.

Using the procedure above, tablets are similarly prepared containing 2-amino-5-bromo-6-metafluorophenyl-4(3H)-pyrimidinone in 250 mg and 100 mg amounts by substituting 250 gm and 10 gm of 2-amino-5-bromo-6-metafluorophenyl-4(3H)-pyrimidinone for the 500 gm used above.

EXAMPLE 4: Oral Suspension

One thousand ml of an aqueous suspension for oral use, containing each teaspoonful (5 ml) dose, 500 mg of 2-amino-5-bromo-6-metafluorophenyl-4(3H)-pyrimidinone, is prepared from the following types and amounts of ingredients:

| | |
|---|---|
| 2-Amino-5-bromo-6-metafluorophenyl-4(3H)-pyrimidinone, micronized | 100 gm |
| Citric acid | 2 gm |
| Benzoic acid | 1 gm |
| Sucrose | 700 gm |
| Tragacanth | 5 gm |
| Lemon Oil | 2 gm |
| Deionized water, q.s. | 1000 ml |

The citric acid, benzoic acid, sucrose, tragacanth and lemon oil are dispersed in sufficient water to make 850 ml of suspension. The 2-amino-5-bromo-6-metafluorophenyl-4(3H)-pyrimidinone, finely divided by means of an air micronizer, is stirred into the syrup until uniformly distributed. Sufficient water is added to make 1000 ml.

The composition so prepared is useful for treating hypertension at a dose of 1 tablespoonful (15 ml) three times a day.

EXAMPLE 5: Parenteral Injection

A sterile aqueous suspension for parenteral injection, containing in 1 ml, 300 mg of 2-amino-5-bromo-6-metafluorophenyl-4(3H)-pyrimidinone, is prepared from the following types and amounts of ingredients:

| | |
|---|---|
| 2-Amino-5-bromo-6-metafluorophenyl-4(3H)-pyrimidinone, micronized | 300 gm |
| Polysorbate 80 | 5 gm |
| Methylparaben | 2.5 gm |
| Propylparaben | 0.17 gm |
| Water for injection, q.s. | 1000 ml |

All the ingredients, except the 2-amino-5-bromo-6-metafluorophenyl-4(3H)-pyrimidinone, are dissolved in the water and the solution sterilized by filtration. To the sterile solution is added the sterilized 2-amino-5-bromo-6-metafluorophenyl-4(3H)-pyrimidinone, finely divided by means of an air micronizer, and the final suspension is filled into sterile vials and the vials sealed.

The composition so prepared is useful for treating hypertension formation at a dose of 1 milliliter (1 ml) three times a day.

EXAMPLE 6: Suppository, Rectal and Vaginal

One thousand suppositories, each weighing 2.5 gm and containing 150 mg of 2-amino-5-bromo-6-metafluorophenyl-4(3H)-pyrimidinone are prepared from the following types and amounts of ingredients:

| | |
|---|---|
| 2-Amino-5-bromo-6-metafluorophenyl-4(3H)-pyrimidinone, micronized | 150 gm |
| Propylene glycol | 150 gm |
| Polyethylene glycol, 4000, q.s. | 2,500 gm |

The 2-amino-5-bromo-6-metafluorophenyl-4(3H)-pyrimidinone is finely divided by means of an air micronizer and added to the propylene glycol and the mixture passed through a colloid mill until uniformly dispersed. The polyethylene glycol 4000 is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for treating hypertension.

EXAMPLE 7: Intranasal Suspension

One thousand ml of a sterile aqueous suspension for intranasal instillation containing in each ml 150 mg of 2-amino-5-bromo-6-metafluorophenyl-4(3H)-pyrimidinone is prepared from the following types and amounts of ingredients:

| | |
|---|---|
| 2-Amino-5-bromo-6-metafluorophenyl-4(3H9-pyrimidinone, mecronized | 150 gm |
| Polysorbate 80 | 5 gm |
| Methylparaben | 2.5 gm |
| Propylparaben | 0.17 gm |
| Deionized water, q.s. | 1000 ml |

All the ingredients, except the 2-amino-5-bromo-6-metafluorophenyl-4(3H)-pyrimidinone, are dissolved in the water and the solution sterilized by filtration. To the sterile solution is added the sterilized 2-amino-5-bromo-6-metafluorophenyl-4(3H)-pyrimidinone, finely divided by means of an air micronizer, and the final suspension is aseptically filled into sterile containers.

The composition so prepared is useful for treating hypertension by intranasal instillation of 0.2 ml to 0.5 ml given one to four times per day.

EXAMPLE 8: Animal Feed

One thousand grams of feed premix is prepared from the following types and amounts of ingredients:

| | |
|---|---|
| 2-Amino-5-bromo-6-metafluorophenyl-4(3H)-pyrimidinone, micronized | 20 gm |
| Soybean meal | 400 gm |
| Fish meal | 400 gm |
| Wheat germ oil | 50 gm |
| Sorghum molasses | 130 gm |

The ingredients are mixed together and pressed into pellents.

The premix can be fed to laboratory animals directly, i.e., rats, and mice for treating hypertension.

For larger animals the premix can be added to the animal's regular feed in an amount calculated to give the desired dose of 2-amino-5-bromo-6-metafluorophenyl-4(3H)-pyrimidinone. For example, one part of premix is added to 2.5 parts of a cat's regular feed to provide the desired dose of 200 mg/kg day for a cat of 2.5 kg.

An active ingredient can also be present, as shown in Examples 9 through 12 in the undiluted pure form for use locally about the cutis, intranasally, pharyngolaryngeally, bronchially, broncholially, or orally.

EXAMPLE 9: Powder

Five hundred grams of 2-amino-5-bromo-6-metafluorophenyl-4(3H)-pyrimidinone in bulk form is finely divided by means of an air micronizer. The micronized powder is placed in a shaker-type container.

The foregoing composition is useful for treating hypertension formation at localized sites by applying the powder one to four per day.

EXAMPLE 10: Oral Powder

One thousand grams of 2-amino-5-bromo-6-metafluorophenyl-4(3H)-pyrimidinone in bulk form is finely divided by means of an air micronizer. The micronized powder is divided into individual doses of 250 mg and packaged.

The foregoing powders are useful for treating hypertension by the oral administration of one or two powders suspended in a glass of water, one to four times per day.

EXAMPLE 11: Insufflation

One thousand grams of 2-amino-5-bromo-6-metafluorophenyl-4(3H)-pyrimidinone in bulk form is finely divided by means of an air micronizer.

The foregoing composition is useful for treating hypertension by the inhalation of 30 to 75 mg, one to four times per day.

EXAMPLE 12: Hard Gelatin Capsules

One thousand two piece hard gelatin capsules for oral use, each capsule containing 100 mg of 2-amino-5-bromo-6-metafluorophenyl-4(3H)-pyrimidinone, are prepared from 100 grams of 2-amino-5-bromo-6metafluorophenyl-4(3H)-pyrimidinone.

The 2-amino-5-bromo-6-metafluorophenyl-4(3H)-pyrimidinone is finely divided by means of an air micronizer and encapsulated in the usual manner.

The foregoing capsules are useful for treating hypertension by the oral administration of one or two capsules, one to four times a day.

Using the procedure above, capsules are similarly prepared containing 2-amino-5-bromo-6-metafluorophenyl-4(3H)-pyrimidinone in 50 mg, 250 mg, and 500 mg amounts by substituting 50 gm, 250 gm, and 500 gm of 2-amino-5-bromo-6-metafluorophenyl-4(3H)-pyrimidinone for the 100 gm used above.

EXAMPLE 13

Following the procedure of the preceding Examples 1 through 12, inclusive, compositions are prepared substituting equivalent amounts of the pharmaceutically acceptable acid addition salts of 2-amino-5-bromo-6-metafluorophenyl-4(3H)-pyrimidinone for the free base of the examples.

EXAMPLE 14

Following the procedure of the preceding Examples 1 through 13 inclusive, compositions are prepared substituting equivalent amounts of 2-amino-5-bromo-6-metafluorophenyl-4(3H)-pyrimidinone or the pharmaceutically acceptable acid addition salts or the alkali metal or alkaline earth metal salts of each of the foregoing compounds for 2-amino-5-bromo-6-metafluorophenyl-4(3H)-pyrimidinone of each of the examples. Those compositions are useful for treating hypertension where administered as described above and in Examples 1 through 13. inclusive.

EXAMPLE 15

Following the procedure of the preceding Examples 1 through 14 compositions are prepared substituting equivalent amounts of other compounds within the scope of formula 1 for the 2-amino-5-bromo-6-metafluorophenyl-4(3H)-pyrimidinone, the preferred or best mode contemplated, of the examples.

We claim:

1. A process for treating hypertension comprising the systemic administering to a hypertensive subject an effective anti-hypertensive amount of a compound of the formula:

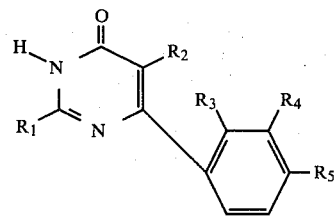

wherein $R_1$ is —$NH_2$.

$R_2$ is chloro, bromo, or iodo.

$R_3$ is hydrogen or fluorine.

$R_4$ is hydrogen or fluorine, and $R_5$ is hydrogen, fluorine, or $CH_3$; or a salt thereof in association with a pharmaceutical carrier.

2. The process of claim 1 wherein the amount administered is from 0.1 mg to 400 mg/kg of body weight.

3. The process of claim 2 wherein the compound is 2-amino-5-bromo-6-metafluorophenyl-4(3H)-pyrimidinone or a salt thereof.

* * * * *